United States Patent
Jödecke et al.

(10) Patent No.: US 8,766,010 B2
(45) Date of Patent: Jul. 1, 2014

(54) METHOD FOR DISTILLING MIXTURES COMPRISING ETHYLENEDIAMINE, N-METHYLETHYLENEDIAMINE, AND WATER, AND MIXTURES OF ETHYLENEDIAMINE AND N-METHYLETHYLENEDIAMINE HAVING A LOW CONTENT OF N-METHYLETHYLENEDIAMINE OBTAINABLE THEREBY

(75) Inventors: Michael Jödecke, Kapellen (BE); Jörg Pastre, Bensheim (DE); Randolf Hugo, Dirmstein (DE)

(73) Assignee: BASF SE (DE)

( * ) Notice: Subject to any disclaimer, the term of this patent is extended or adjusted under 35 U.S.C. 154(b) by 37 days.

(21) Appl. No.: 13/513,363

(22) PCT Filed: Nov. 30, 2010

(86) PCT No.: PCT/EP2010/068469
§ 371 (c)(1),
(2), (4) Date: Jun. 1, 2012

(87) PCT Pub. No.: WO2011/067226
PCT Pub. Date: Jun. 9, 2011

(65) Prior Publication Data
US 2012/0253077 A1    Oct. 4, 2012

(30) Foreign Application Priority Data

Dec. 2, 2009  (EP) .................................. 09177776

(51) Int. Cl.
*C07C 209/84*  (2006.01)
*C07C 209/86*  (2006.01)

(52) U.S. Cl.
USPC ......................................... 564/499; 564/498

(58) Field of Classification Search
USPC .............................................. 564/498, 499
See application file for complete search history.

(56) References Cited

U.S. PATENT DOCUMENTS

| 3,126,383 A * | 3/1964 | Cooper .......................... 544/358 |
| 4,032,411 A | 6/1977 | Tornquist et al. |
| 2007/0100144 A1 | 5/2007 | Frauenkron et al. |

FOREIGN PATENT DOCUMENTS

| WO | WO-2005014523 A1 | 2/2005 |
| WO | WO-2010042168 A2 | 4/2010 |

OTHER PUBLICATIONS

Eller, Karsten, et al., "Amines, Aliphatic", Ullmann's Encyclopedia of Industrial Chemistry, 6th Edition, Jan. 1, 2002, pp. 1-54.
International Search Report for PCT/EP2010/068469, mailed Apr. 1, 2011.
Translation of the International Preliminary Report on Patentability for PCT/EP2010/068469 dated Jun. 5, 2012.

* cited by examiner

*Primary Examiner* — Brian J Davis
(74) *Attorney, Agent, or Firm* — Drinker Biddle & Reath LLP

(57) ABSTRACT

The present invention relates to a mixture of ethylenediamine (EDA) and N-methylethylenediamine (Me-EDA) with a low content of Me-EDA, which comprises at least 99.5% by weight of ethylenediamine, and wherein the concentration of N-methylethylenediamine is in the range from 0.005 to 0.15% by weight.
The present invention further relates to a process for distillative workup of a mixture comprising EDA, Me-EDA and water, by introducing the mixture into a distillation column which is operated at a column top pressure of 10 mbar to 4 bar, wherein the weight ratio of water to ethylenediamine in the mixture used is a*X:Y where X is the proportion by weight of water and Y is the proportion by weight of ethylenediamine at the azeotropic point of a binary mixture of water and ethylenediamine at the column top pressure in question, and a is a real number with a value of 0.9 or more.
The present invention further provides a process for preparing a distillable mixture comprising EDA, Me-EDA and water, which is suitable for preparing EDA with a low Me-EDA content.

12 Claims, No Drawings

METHOD FOR DISTILLING MIXTURES COMPRISING ETHYLENEDIAMINE, N-METHYLETHYLENEDIAMINE, AND WATER, AND MIXTURES OF ETHYLENEDIAMINE AND N-METHYLETHYLENEDIAMINE HAVING A LOW CONTENT OF N-METHYLETHYLENEDIAMINE OBTAINABLE THEREBY

CROSS-REFERENCE TO RELATED APPLICATIONS

This application is a national stage application (under 35 U.S.C. §371) of PCT/EP2010/068469, filed Nov. 30, 2010, which claims benefit of European Application No. 09177776.3, filed Dec. 2, 2009.

The present invention relates to a mixture of ethylenediamine (EDA) and N-methylethylenediamine (Me-EDA) with a low content of Me-EDA. The present invention further relates to a process for distillative workup of a mixture comprising EDA, Me-EDA and water, and to a process for preparing a distillable mixture comprising EDA, Me-EDA and water, which is suitable for preparing EDA with a low Me-EDA content.

Ethylenediamine (=diaminoethane) is used predominantly as an intermediate for the production of bleach activators, crop protection compositions, pharmaceuticals, lubricants, textile resins, polyamides, papermaking assistants or gasoline additives.

Numerous processes are known for preparing ethylenediamine (EDA) (see, for example, Ullmann's Encyclopedia of Industrial Chemistry, "Amines, Aliphatic", section 8.1.1, DOI: 10.1002/14356007.a02_001).

In the preparation of ethylenediamine, N-methylethylenediamine (Me-EDA) can be formed by side reactions.

For example, in the reaction of monoethanolamine (MEOA) with ammonia to give EDA, a degradation reaction of monoethanolamine can directly form carbon monoxide (CO) and methylamine (decarbonylation). The methylamine can in turn react directly with further monoethanolamine to give Me-EDA.

Me-EDA can also form in the dimerization of monoethanolamine to give aminoethylethanolamine (AEEA) when AEEA is degraded directly by decarbonylation to Me-EDA.

Me-EDA can also form in the preparation of ethylenediamine from C1 units, such as hydrogen cyanide and formaldehyde.

For most industrial applications, the market requires a purity of EDA of at least 99.5% by weight. Organic secondary components including Me-EDA may be present with a maximum proportion of 0.5% by weight. In addition, the water content may be a maximum of 0.5% by weight.

Especially in the case of EDA preparation processes based on monoethanolamine or C1 units such as hydrogen cyanide and formaldehyde, a content of less than 0.5% by weight of Me-EDA generally cannot be achieved if the capital and production costs are to remain within an economic range.

An increase in the proportion of Me-EDA can also occur with increasing service life and deactivation of the catalyst which is used for the EDA preparation, since the reaction temperature is generally increased to compensate for the lower activity of the catalyst, and hence the formation of undesired by-products increases.

EDA which comprises a relatively high Me-EDA content as a result of the preparation must correspondingly be worked up such that a proportion of 0.5% by weight of organic secondary components and 0.5% by weight of water is not exceeded as per the specification.

Me-EDA and EDA form a close-boiling azeotropic mixture at standard pressure, which generally cannot be separated with a technically acceptable level of complexity.

In the separation of water and EDA, there is generally only a slight depletion of Me-EDA, for instance in the region of a few 10ths of one percent.

Since small amounts of Me-EDA and water can be removed from EDA only with very great difficulty, it is generally impossible in practice to use EDA with a relatively high Me-EDA content.

It is an object of the present invention to provide a process for purifying EDA, with which EDA can be processed to give on-spec products from processes in which a relatively high proportion of Me-EDA is obtained as a result of the preparation. This process should be implementable with low capital costs and operable with low production costs.

It is a further object of the present invention to provide a mixture of EDA and Me-EDA with a low proportion of Me-EDA.

This technical object is achieved by a process for distilling a mixture comprising water, ethylenediamine and methylethylenediamine, by introducing the mixture into a distillation column which is operated at a column top pressure of 10 mbar to 4 bar, wherein the weight ratio of water to ethylenediamine in the mixture used is $a*X:Y$ where X is the proportion by weight of water and Y is the proportion by weight of ethylenediamine at the azeotropic point of a binary mixture of water and EDA at the column top pressure in question, and a is a real number with a value of 0.9 or more.

In the process according to the invention, mixtures comprising ethylenediamine, N-methylethylenediamine and water are used.

According to the invention, the weight ratio of water to EDA in the mixture which is used in the process according to the invention is $a*X:Y$ where X is the proportion by weight of water and Y is the proportion by weight of ethylenediamine at the azeotropic point of a binary mixture of water and EDA at the column top pressure in question, and a is a real number with a value of 0.9 or more, preferably 1.0 or more and more preferably 1.02 or more.

Hereinafter, mixtures comprising EDA, water and Me-EDA, in which the weight ratio of water to EDA is $a*X:Y$ where X is the proportion by weight of water and Y is the proportion by weight of ethylenediamine at the azeotropic point of a binary mixture of water and EDA at the column top pressure in question, and a is a real number with a value of 0.9 or more, preferably 1.0 or more and more preferably 1.02 or more, are referred to as "distillable mixtures".

When the weight ratio of water to EDA in the mixture to be distilled is $a*X:Y$ where X is the proportion by weight of water and Y is the proportion by weight of ethylenediamine at the azeotropic point of a binary mixture of water and EDA at the column top pressure in question, and a is a real number with a value of less than 0.9, water additionally has to be added to the mixture to be distilled before it is used in the process according to the invention such that the weight ratio of water to EDA in the mixture is $a*X:Y$ where X is the proportion by weight of water and Y is the proportion by weight of ethylenediamine at the azeotropic point of a binary mixture of water and EDA at the column top pressure in question, and a is a real number with a value of 0.9 or more, preferably 1.0 or more and more preferably 1.02 or more.

"Mixtures to be distilled" accordingly refer to mixtures comprising EDA, water and Me-EDA, in which the weight ratio of water to EDA is $a*X:Y$ where X is the proportion by weight of water and Y is the proportion by weight of ethylenediamine at the azeotropic point of a binary mixture of water and EDA at the column top pressure in question, and a is a real number with a value of less than 0.9.

According to the invention, mixtures to be distilled can be converted by adding water to a distillable mixture.

Accordingly, the present invention also relates to a process for preparing a distillable mixture comprising EDA and Me-EDA, which comprises adding a sufficient amount of water to a mixture comprising EDA and Me-EDA to be distilled that, after the addition of water, the weight ratio of EDA to water is a*X:Y where X is the proportion by weight of water and Y is the proportion by weight of ethylenediamine at the azeotropic point of a binary mixture of water and EDA at the column top pressure at which the subsequent inventive distillation of the intermediate can be effected, and a is a real number with a value of 0.9 or more, preferably 1.0 or more and more preferably 1.02 or more.

The water content of a mixture comprising EDA, Me-EDA and water can be determined by means of the customary methods of determining water, for example by Karl Fischer titration.

Water is typically supplied by means of a metering pump, preferably continuously.

The amount of water required to prepare a distillable mixture is selected such that, after the addition of water, the weight ratio of EDA to water is a*X:Y where X is the proportion by weight of water and Y is the proportion by weight of ethylenediamine at the azeotropic point of a binary mixture of water and EDA at the column top pressure in question, and a is a real number with a value of 0.9 or more, preferably 1.0 or more and more preferably 1.02 or more.

The maximum amount of water added is generally selected such that the removal of the additionally added water is within an economic range, since the removal of water can increase both the apparatus complexity and the energy expenditure in the distillation.

More preferably, after the addition of water, the weight ratio of EDA to water is a*X:Y where X is the proportion by weight of water and Y is the proportion by weight of ethylenediamine at the azeotropic point of a binary mixture of water and EDA at the column top pressure in question, at which the subsequent distillation of the distillable mixture is effected, and a is a real number with a value of 0.9 to 2.0, preferably 1.0 to 1.5, more preferably 1.01 to 1.2 and especially preferably 1.02 to 1.1.

The determination of the proportion by weight of water at the azeotropic point of a binary mixture of water and EDA as a function of pressure is familiar to the person skilled in the art.

For instance, azeotropic points can be determined experimentally as a function of pressure, the methods being known to the person skilled in the art. Azeotropic points for the binary EDA and water system can be found, for example, in the book "Azeotropic Data Part I" (J. Gmehling, J. Menke, J. Krafczyk, K. Fischer, Wiley-VCH, 2004, page 425).

In addition, the position of the binary mixture of EDA and water—i.e. a compilation of the experimentally determined values—is likewise described in the relevant literature (see "Azeotropic Data Part I" by J. Gmehling, J. Menke, J. Krafczyk, K. Fischer, Wiley-VCH, 2004, page 425 or "Dortmund Data Bank" (http://www.ddbst.de/new/Default.htm)).

The proportion by weight of water at the azeotropic point can additionally be calculated in a good approximation with activity coefficient models such as NRTL. This method is implemented as standard in commercial simulation programs, such as Aspen Plus® from Aspentech. The abovementioned sources for mixture data also report calculation parameters, for example NRTL parameters, with the aid of which the azeotropic point can also be calculated at least in a good approximation for pressures different than the figures.

The proportion by weight of water at the azeotropic point is preferably calculated by means of the NRTL model from Aspen. The calculation generally uses an ideal gas phase. If the calculation uses a real gas phase, this is mentioned in the abovementioned sources for the mixture data. The vapor pressure curves for EDA and water can be found in the Dortmund Data Bank, other sources or other literature. This allows the azeotropic point of EDA and water to be calculated as a function of pressure.

The proportion by weight of water at the azeotropic point, which is calculated on the basis of models such as NRTL, can differ from the experimentally determined azeotropic composition within a certain error limit.

What is crucial for the calculation of the amount of water to be added is, however, the actual proportion by weight of water at the azeotropic point which occurs in reality.

When the weight ratio of water to EDA in the distillable mixture is a*X:Y where X is the proportion by weight of water and Y is the proportion by weight of ethylenediamine at the azeotropic point of a binary mixture of water and EDA at the column top pressure in question, and a is a real number in the range from 0.9 to 1.0, in a preferred embodiment, water is additionally added to the distillable mixture such that a preferred distillable mixture is obtained, in which the proportion by weight of water to EDA in the mixture is a*X:Y where X is the proportion by weight of water and Y is the proportion by weight of ethylenediamine at the azeotropic point of a binary mixture of water and EDA at the column top pressure in question, and a is a real number with a value of 1.0 or more and preferably 1.02 or more.

In this preferred embodiment, the maximum amount of water added, as described above, is likewise generally selected such that the removal of the additionally added water is within an economic range, since the removal of water can increase both the apparatus complexity and the energy expenditure in the distillation.

In this preferred embodiment, after the addition of water, the weight ratio of water to EDA is preferably a*X:Y, where X is the proportion by weight of water and Y is the proportion by weight of ethylenediamine at the azeotropic point of a binary mixture of water and EDA at the column top pressure in question, at which the subsequent distillation of the distillable mixture is effected, and a is a real number with a value of 1.0 to 1.5, preferably 1.01 to 1.2 and more preferably 1.02 to 1.1.

In the mixtures which are used in the distillation process according to the invention or in the process according to the invention for preparing distillable mixtures, the weight ratio of EDA to Me-EDA is preferably 1:0.003 to 1:0.2, more preferably 1:0.005 to 1:0.1 and most preferably 1:0.01 to 1:0.05.

Mixtures which are used in the distillation process according to the invention or in the process according to the invention for preparing a distillable mixture may comprise additional components such as higher-boiling amines, unconverted starting materials and organic by-products. Higher-boiling amines are understood hereinafter to mean amines which have a higher boiling point than EDA at the same pressure, for example piperazine (PIP), monoethanolamine, diethylenetriamine, aminoethylethanolamine, triethylenetetramine (TETA) and higher ethyleneamines (i.e. ethyleneamines with a higher boiling point than TETA).

The weight ratio of the abovementioned components in these mixtures is preferably:
EDA:water=1:0.05 to 0.8;
EDA:Me-EDA=1:0.003 to 0.2;
EDA:ammonia=1:0 to 0.05;
EDA:higher-boiling amines=1:0 to 1.25; and
EDA:organic by-products=1:0 to 0.05;
and more preferably:
EDA:water=1:0.1 to 0.5;
EDA:Me-EDA=1:0.005 to 0.05;
EDA:ammonia=1:0 to 0.025;
EDA:higher-boiling amines=1:0.05 to 1; and
EDA:organic by-products=1:0.0001 to 0.025.

Mixtures comprising ethylenediamine, N-methylethylenediamine and water, which can be used in the distillation process according to the invention or in the process according to the invention for preparing a distillable mixture, comprise preferably less than 5% by weight of ammonia, more preferably less than 2% by weight of ammonia, more preferably less than 1% by weight of ammonia and especially preferably less than 0.5% by weight of ammonia.

Mixtures which can be used in the distillation process according to the invention or in the process according to the invention for preparing a distillable mixture are preferably obtained by removing hydrogen and/or ammonia from a reaction discharge obtained in the preparation of EDA.

Such a reaction discharge can be obtained, for example, by reacting MEOA with ammonia or reacting ethylene oxide with ammonia or reacting formaldehyde, hydrogen cyanide, ammonia and hydrogen.

The reaction of MEOA and ammonia is described, for example, in U.S. Pat. No. 2,861,995, DE-A-1 172 268 and U.S. Pat. No. 3,112,318. An overview of the different process variants of the reaction of MEOA with ammonia can be found, for example, in the PERP Report No. 138 "Alkyl-Amines", SRI International, 03/1981 (especially pages 81-99, 117). The reaction of monoethanolamine with ammonia is preferably performed in a fixed bed reactor over a transition metal catalyst at 150-250 bar and 160-210° C., or over a zeolite catalyst at 1-20 bar and 280-380° C.

Transition metal catalysts used with preference comprise Ni, Co, Cu, Ru, Re, Rh, Pd or Pt, or a mixture of two or more of these metals, on an oxidic support (e.g. $Al_2O_3$, $TiO_2$, $ZrO_2$, $SiO_2$).

Preferred zeolite catalysts are mordenites, faujasites and chabazites.

To achieve a maximum EDA selectivity, the transition metal catalysis is generally conducted with a molar ratio of ammonia to monoethanolamine of 6-20, preferably 8-15, and in the case of zeolite catalysis of generally 20-80, preferably 30-50.

The MEOA conversion is generally held in the range between 10% and 80%, preferably 40-60%.

In continuous operation, a catalyst hourly space velocity in the range of 0.3-0.6 kg/(kg*h) (kg of MEOA per kg of cat. per hour) is preferably established.

To maintain the catalyst activity, in the case of use of metal catalysts, 0.05-0.5% by weight (based on the reaction input of MEOA+$NH_3$+$H_2$) of hydrogen is preferably additionally conducted into the reactor.

A further route for preparing a reaction discharge is the direct reaction of ethylene oxide with ammonia, which is described, for example, in Eur. Chem. News 20 (1971) No. 495, 16 and the abovementioned PERP-Report.

A reaction discharge can also be prepared by the reaction of formaldehyde, hydrogen cyanide, ammonia and hydrogen.

For instance, U.S. Pat. No. 2,519,803 describes a process for preparing ethylenediamine by the hydrogenation of a partly purified aqueous reaction mixture which results from an amination of formaldehyde cyanohydrin (FACH), and comprises aminoacetonitrile as an intermediate. Formaldehyde cyanohydrin can in turn be obtained by reaction of formaldehyde with hydrogen cyanide. A process description for preparation of FACH can be found, for example, in the application PCT/EP2008/052337, page 26, and in the application WO-A1-2008/104582, page 30 (variants a) and b)), to which explicit reference is made at this point.

DE-A 1 154 121 relates to a further process for preparing ethylenediamine, wherein the hydrogen cyanide, formaldehyde, ammonia and hydrogen reactants are reacted in a one-pot process in the presence of a catalyst.

WO-A1-2008/104592 relates to a process for preparing EDA by hydrogenating aminoacetonitrile. Aminoacetonitrile is typically obtained by reacting formaldehyde cyanohydrin with ammonia, and formaldehyde cyanohydrin is in turn generally prepared from hydrogen cyanide and ammonia.

Preference is given to preparing a reaction discharge comprising EDA and Me-EDA by the process described in WO-A-2008/104592, to which explicit reference is hereby made.

The reaction discharges which are prepared by the above-described reactions generally comprise hydrogen, which is generally removed by decompressing the reaction discharge, for example to 20 to 30 bar.

After the removal of hydrogen, the reaction discharges which are obtained in the preparation of EDA generally comprise EDA, water, Me-EDA, ammonia and generally higher-boiling amines, and also unconverted feedstocks and organic by-products.

In a preferred embodiment, the reaction discharges have a relatively high content of Me-EDA.

Such reaction discharges are preferably obtained when EDA is prepared from C1 units, such as formaldehyde and hydrogen cyanide, or when the catalyst which is used to prepare EDA loses activity, for example after increasing operating time, and this loss of activity is compensated for by increasing the reaction temperature at the expense of the EDA selectivity.

In the preferred embodiment in which the reaction discharges from the EDA preparation have a relatively high content of Me-EDA, the weight ratio of EDA to Me-EDA in the reaction discharge which is obtained in the preparation of EDA is preferably 1:0.003 to 1:0.2, more preferably 1:0.005 to 1:0.1 and most preferably 1:0.01 to 1:0.05.

The weight ratio of the components in the reaction discharge is preferably:
EDA:water=1:0.05 to 0.8;
EDA:Me-EDA=1:0.003 to 0.2;
EDA:ammonia=1:0.002 to 20;
EDA:higher-boiling amines=1:0 to 1.25; and
EDA:organic by-products=1:0 to 0.05.

In a particularly preferred embodiment, the reaction discharges are obtained by reaction of MEOA and ammonia, where the weight ratio of the components in the reaction discharge is:
EDA:water=1:0.1 to 0.5;
EDA:Me-EDA=1:0.005 to 0.1;
EDA:ammonia=1:3 to 15;
EDA:higher-boiling amines=1:0.01 to 1.0; and
EDA:organic by-products=1:0.0001 to 0.025
and most preferably:
EDA:water=1:0.1 to 0.5;
EDA:Me-EDA=1:0.01 to 0.05;

EDA:ammonia=1:3 to 15;
EDA:higher-boiling amines=1:0.05 to 1:0.5; and
EDA:organic by-products=1:0.0001 to 0.01.

In a further particularly preferred embodiment, the reaction discharges are obtained by reaction of formaldehyde, hydrogen cyanide, ammonia and hydrogen, where the weight ratio of the components in the reaction discharge is:
EDA:water=1:0.1 to 0.5;
EDA:Me-EDA=1:0.005 to 0.1;
EDA:ammonia=1:0.005 to 0.1;
EDA:higher-boiling amines=1:0.01 to 1:1.0; and
EDA:organic by-products=1:0.0001 to 0.025
and most preferably:
EDA:water=1:0.1 to 0.5;
EDA:Me-EDA=1:0.01 to 0.05;
EDA:ammonia=1:0.01 to 0.05;
EDA:higher-boiling amines=1:0.05 to 1:0.5; and
EDA:organic by-products=1:0.0001 to 0.01.

In addition to the preferred use of reaction discharges which have a relatively high content of Me-EDA, it is possible to use reaction discharges which comprise EDA, Me-EDA and water and have a lower Me-EDA content in the process according to the invention, such that a further lowering in the proportion of Me-EDA can be achieved.

After the removal of hydrogen, the reaction discharges from the different EDA preparation routes typically comprise, as well as EDA, Me-EDA and water, additionally ammonia.

The ammonia is generally removed from reaction discharges comprising EDA and Me-EDA in a distillation column.

The exact operating conditions of the distillation column can be determined according to the separating performance of the column used by the person skilled in the art with reference to the known vapor pressures and evaporation equilibria of the components introduced into the distillation column in routine manner by conventional calculation methods.

The ammonia is preferably removed in a pressure column, the column pressure being selected such that the ammonia can be condensed with the cooling medium present at the given cooling medium temperature, for example cooling water. The ammonia is preferably removed in a distillation column which has internals for increasing the separating performance.

The ammonia removal is more preferably performed in a tray column since such columns are very suitable for operation at high pressure and are less expensive than columns with structured packings.

In a tray column, there are intermediate trays within the column, on which the mass transfer takes place. Examples of different tray types are sieve trays, tunnel-cap trays, dual-flow trays, bubble-cap trays or valve trays.

The distillative internals may, however, also be present in the form of a structured packing, for example as a sheet metal packing, such as MELLAPAK™ 250 Y sheet metal packing or Montz Pak, B1-250 type, or as a structured ceramic packing, or as a random packing, for example composed of Pall rings, IMTP rings (from Koch-Glitsch), Raschig Superrings, etc. Structured or random packings may be arranged in one bed or preferably in a plurality of beds.

The reaction discharge comprising EDA and Me-EDA is preferably supplied in a spatial region between 30% and 90% of the theoretical plates of the distillation column (counted from the bottom), more preferably in a spatial region between 50% and 80% of the theoretical plates of the distillation column. For example, the supply can be effected somewhat above the middle of the theoretical plates. The optimal feed site can be determined by the person skilled in the art as a function of the ammonia concentration with the customary calculation tools.

The number of theoretical plates is generally in the range from 5 to 30, preferably 10 to 20.

The top pressure is more preferably 1 to 30 bar, more preferably 10 to 20 bar.

In the column bottom, a temperature above the evaporation temperature of the ammonia is preferably established, such that ammonia is converted substantially or very substantially to the gas phase.

Particular preference is given to establishing a temperature which corresponds virtually to the boiling temperature of the mixture to be removed via the bottom at column bottom pressure. The temperature depends on the type and composition of the substances present in the bottom product, and can be determined by the person skilled in the art with the customary thermodynamic calculation tools. For example, at a column top pressure of 18 bar, it is preferably possible to establish a column bottom temperature of 220 to 260° C., more preferably of 230 to 250° C.

The condenser of the distillation column is generally operated at a temperature at which the predominant portion of the ammonia is condensed at the corresponding top pressure. In general, the operating temperature of the condenser is in the range from 30 to 70° C., preferably 35 to 50° C.

The return at the top of the column is generally adjusted such that the predominant amount of the amines and water are retained in the column, such that they are obtained virtually completely as the bottom product. The condensate obtained in the condenser is preferably recycled to an extent of more than 30%, preferably to an extent of more than 49%, into the top of the distillation column.

The energy required for the evaporation is typically introduced by means of an evaporator in the column bottom.

In the condenser, predominantly ammonia is obtained as the condensate.

The ammonia obtained as the condensate can be used after a purification or preferably directly as starting material for further chemical syntheses. For example, the ammonia obtained as a condensate can be reused to prepare ethylenediamine, by recycling the ammonia to the ethylenediamine preparation process.

The bottoms discharge obtained from the ammonia removal is generally a mixture which comprises EDA, water and Me-EDA, and generally higher-boiling amines and organic by-products.

When the weight ratio of water to EDA in the mixture is a*X:Y where X is the proportion by weight of water and Y is the proportion by weight of ethylenediamine at the azeotropic point of a binary mixture of water and EDA at the column top pressure in question, and a is a real number with a value of less than 0.9, water additionally has to be added, as explained above, to the mixture to be distilled, before it is used in the process according to the invention, such that the weight ratio of water to EDA in the mixture used in the process according to the invention is a*X:Y where X is the proportion by weight of water and Y is the proportion by weight of ethylenediamine at the azeotropic point of a binary mixture of water and EDA at the column top pressure in question, and a is a real number with a value of 0.9 or more, preferably 1.0 or more and more preferably 1.02 or more.

When the weight ratio of water to EDA in the mixture is a*X:Y where X is the proportion by weight of water and Y is the proportion by weight of ethylenediamine at the azeotropic point of a binary mixture of water and EDA at the column top pressure in question, and a is a real number with a value of 0.9 or more, preferably 1.0 or more and more preferably 1.02 or more, the mixture is a distillable mixture which, as described above, can be used directly in the distillation process according to the invention.

When the weight ratio of water to EDA in the distillable mixture is a*X:Y where X is the proportion by weight of water and Y is the proportion by weight of ethylenediamine at the azeotropic point of a binary mixture of water and EDA at the column top pressure in question, and a is a real number in the range from 0.9 to 1.0, in a preferred embodiment, water is additionally added, as described above, to the distillable mixture so as to obtain a preferred distillable mixture in which the proportion by weight of water to EDA in the mixture is a*X:Y where X is the proportion by weight of water and Y is the proportion by weight of ethylenediamine at the azeotropic point of a binary mixture of water and EDA at the column top pressure in question, and a is a real number with a value of 1.0 or more and preferably 1.02 or more.

According to the invention, a distillable mixture comprising EDA, Me-EDA and water, in which the weight ratio of water to EDA is a*X:Y where X is the proportion by weight of water and Y is the proportion by weight of ethylenediamine at the azeotropic point of a binary mixture of water and EDA at the column top pressure in question, and a is a real number with a value of 0.9 or more, preferably 1.0 or more and more preferably 1.02 or more, is introduced into a distillation column (Me-EDA removal).

The distillation column preferably has internals for increasing the separating performance. The distillative internals may preferably be present as a structured packing, for example as sheet metal packings such as MELLAPAK™ 250 Y sheet metal packings or Montz Pak, B1-250 type. It is also possible for a packing with lower or increased specific surface area to be present, or it is possible to use a fabric packing or a packing with another geometry, such as MELLAPAK™ 252.Y sheet metal packings. Advantages in the case of use of these distillative internals are the low pressure drop and the low specific liquid holdup compared to valve trays, for example. The internals may be present in one or more beds.

The distillable mixture comprising EDA, Me-EDA and water is preferably supplied within a spatial region between 25% and 75% of the theoretical plates of the distillation column (counted from the bottom), more preferably within a spatial region between 30% and 65% of the theoretical plates of the distillation column. For example, the supply may be slightly below the middle of the theoretical plates. The optimal feed point can be determined by the person skilled in the art with the customary calculation tools.

The number of theoretical plates is generally in the range from 5 to 50, preferably 20 to 40.

According to the invention, the top pressure is 10 mbar to 4 bar, more preferably 20 mbar to 2 bar and most preferably 50 mbar to 200 mbar.

In a further preferred embodiment, the column is operated at atmospheric pressure, approx. 1 bar, at the top, since a simple apparatus configuration of the distillation can be accomplished at atmospheric pressure.

In the column bottom, preference is given to establishing a temperature which is above the evaporation temperature of water but below the evaporation temperature of the azeotropic binary mixture of EDA and water at the azeotropic point, such that the amount of water which corresponds approximately to the difference between the water concentration of the mixture to be distilled (column input) and the proportion by weight of water at the azeotropic point is converted to the gas phase.

For example, at a column top pressure of 100 mbar, preferably a column bottom temperature of 60 to 90° C., more preferably of 65 to 80° C., can be established.

The condenser of the distillation column is generally operated at a temperature at which the predominant portion of the water is condensed at the corresponding top pressure. In general, the operating temperature of the condenser is in the range from 25 to 70° C., preferably 30 to 50° C.

The condensate obtained in the condenser is preferably recycled to an extent of more than 80%, preferably to an extent of more than 90%, into the top of the distillation column.

The energy required for the evaporation is typically introduced by means of an evaporator in the column bottom.

In the condenser falls as condensate which comprises predominantly water and Me-EDA.

The bottoms discharge obtained is generally a mixture which comprises EDA and water, with or without higher-boiling amines such as piperazine, monoethanolamine, diethylenetriamine, aminoethylethanolamine, triethylenetetramine and higher ethyleneamines.

The ratio of Me-EDA to EDA in the bottoms discharge is preferably lower than the ratio of Me-EDA to EDA in the mixture to be distilled, which is introduced as the input into the Me-EDA removal.

The weight ratio of EDA to Me-EDA in the bottoms discharge from the Me-EDA removal is preferably less than 1:0.003, more preferably less than 1:0.002 and preferably less than 1:0.001. The weight ratio of EDA to Me-EDA in the bottoms discharge from the Me-EDA removal is preferably in the range from 1:0 to 1:0.003, more preferably 1:0.0001 to 1:0.002 and most preferably 1:0.0002 to 1:0.001.

The concentration of Me-EDA in the bottoms discharge can surprisingly be reduced significantly by the distillation of a distillable mixture of Me-EDA, EDA and water in which the weight ratio of water to ethylenediamine in the mixture to be distilled is a*X:Y where X is the proportion by weight of water and Y is the proportion by weight of ethylenediamine at the azeotropic point of a binary mixture of water and EDA at the column top pressure in question, and a is a real number with a value of 0.9 or more. This is all the more surprising in that Me-EDA and EDA are very similar components which form a close-boiling azeotropic mixture. The addition of water apparently increases the volatility of Me-EDA compared to EDA.

The mixture which is obtained as the bottoms discharge from the Me-EDA removal comprises predominantly water and EDA, with or without higher-boiling amines such as piperazine, monoethanolamine, diethylenetriamine, aminoethylethanolamine, triethylenetetramine and higher ethyleneamines.

To reduce the water content, the bottoms discharge from the Me-EDA removal is generally supplied to a further distillation stage ("water removal").

Water is generally removed from the mixture comprising EDA and water in a distillation column which is operated in such a way that predominantly water is obtained at the top of the column, and EDA and the higher-boiling amines can be withdrawn at the bottom of the column.

The exact operating conditions of the distillation column can be determined according to the separating performance of the column used by the person skilled in the art with reference to the known vapor pressures and evaporation equilibria of the components introduced into the distillation column by conventional calculation methods in routine manner.

The water removal is effected in a distillation column which generally has internals for increasing the separating performance.

The water removal is preferably performed in a tray column since such columns are very suitable for operation at high pressure.

In a tray column, there are intermediate trays in the interior of the column, on which the mass transfer takes place. Examples of different tray types are sieve trays, tunnel-cap trays, dual-flow trays, bubble-cap trays or valve trays.

The distillative internals may, however, also be present as a structured packing, for example as a sheet metal packing, such as MELLAPAK™ 250 Y sheet metal packing or Montz Pak, B1-250 type, or as a structured ceramic packing.

The distillable mixture comprising EDA and water is preferably supplied in a spatial region between 40% and 90% of the theoretical plates of the distillation column (counted from the bottom), more preferably in a spatial region between 50% and 75% of the theoretical plates of the distillation column. For example, the supply may be slightly above the middle of the theoretical plates. The optimal feed point can be determined by the person skilled in the art with the customary calculation tools. The number of theoretical plates is generally in the range from 10 to 80, preferably 30 to 60.

The top pressure is more preferably 4 to 30 bar, more preferably 6 to 10 bar. At these pressures, the binary mixture of water and EDA does not form an azeotrope.

In the column bottom, preference is given to establishing a temperature which is above the evaporation temperature of water but below the evaporation temperature of EDA. For example, at a column top pressure of 8 bar (abs.), preferably a column bottom temperature of 180 to 250° C., more preferably of 210 to 230° C., can be established.

The condenser of the distillation column is generally operated at a temperature in which the predominant portion of the water is condensed at the corresponding top pressure. In general, the operating temperature of the condenser is in the range from 150 to 230° C., preferably 160 to 180° C.

The condensate obtained in the condenser is preferably recycled into the top of the distillation column to an extent of more than 50%, preferably to an extent of more than 65%.

The energy required for the evaporation is typically introduced by means of an evaporator in the column bottom.

In the condenser, a condensate which comprises predominantly water is obtained. The water thus obtained can generally be sent directly to disposal, for example by introducing it into a wastewater treatment plant.

The bottoms discharge obtained from the water removal is generally a mixture which comprises EDA, with or without other amines such as piperazine, monoethanolamine, diethylenetriamine, aminoethylethanolamine, triethylenetetramine and higher ethyleneamines.

The bottoms discharge from the water removal preferably comprises less than 0.5% by weight of water, preferably less than 0.4% by weight of water and more preferably less than 0.3% by weight of water.

In general, the bottoms discharge from the water removal comprises, as well as EDA, also amines which have a higher boiling point than EDA at the same pressure, known as "higher-boiling amines", such as piperazine, monoethanolamine, diethylenetriamine, aminoethylethanolamine, triethylenetetramine and higher ethyleneamines.

The higher-boiling amines present in the bottoms discharge from the water removal are generally removed in one or more subsequent distillation stages.

The bottoms discharge from the water removal can be separated in one or more further distillation stages into the corresponding amine-containing fractions.

Typically, the bottoms discharge from the water removal is introduced into a further distillation column (EDA/PIP removal), which is operated in such a way that EDA and piperazine are obtained at the top of the column, and the other higher-boiling amines can be drawn off at the bottom of the column. The exact operating conditions of the distillation column can be determined according to the separating performance of the column used by the person skilled in the art with reference to the known vapor pressures and evaporation equilibria of the components introduced into the distillation column by conventional calculation methods in a routine manner.

The distillation column preferably has internals for increasing the separating performance. The distillative internals may be present, for example, as a structured packing, for example as a sheet metal packing such as MELLAPAK™ 250 Y sheet metal packing or Montz Pak, B1-250 type. It is also possible for a packing with a lower or increased specific surface area to be present, or it is possible to use a fabric packing or a packing with another geometry such as MELLAPAK™ 252 Y sheet metal packing. Advantages in the case of use of these distillative internals are the low pressure drop and the low specific liquid holdup compared to valve trays, for example. The internals may be present in one or more beds.

The bottoms discharge from the water removal is preferably supplied within a spatial region between 25% and 75% of the theoretical plates of the distillation column (counted from the bottom), more preferably within a spatial region between 30% and 65% of the theoretical plates of the distillation column. For example, the supply may be somewhat above the middle of the theoretical plates. The optimal feed point can be determined by the person skilled in the art with the customary calculation tools.

The number of theoretical plates is generally in the range from 30 to 90, preferably 40 to 70.

The top pressure is more preferably 0.1 to 10 bar, more preferably 0.5 to 5 bar. Very particular preference is given to operating the column at standard pressure.

In the column bottom, preference is given to establishing a temperature which is above the evaporation temperature of EDA but below the evaporation temperature of DETA. For example, at a column top pressure of 1 bar (abs.), preferably a column bottom temperature of 170 to 220° C., more preferably of 180 to 210° C., can be established.

The condenser of the distillation column is generally operated at a temperature at which the predominant portion of the EDA-piperazine mixture is condensed at the corresponding top pressure. In general, the operating temperature of the condenser is in the range from 50 to 150° C., preferably 110 to 130° C.

The condensate obtained in the condenser is preferably recycled into the top of the distillation column to an extent of more than 30%, preferably to an extent of more than 50% by weight.

The energy required for the evaporation is typically introduced by means of an evaporator in the column bottom.

The bottoms discharge obtained is generally a mixture which comprises higher-boiling amines such as diethylenetriamine, aminoethylethanolamine, triethylenetetramine and higher ethyleneamines. The bottoms discharge can be separated in further distillation stages into the individual components or individual fractions.

In the condenser, a condensate is obtained, which comprises predominantly EDA and piperazine, but only very small amounts of Me-EDA.

The condensate is generally predominantly free of other higher-boiling amines. The proportion of higher-boiling amines (except piperazine) is generally less than 0.2% by weight, preferably less than 0.1% by weight and more preferably less than 0.05% by weight.

The tops discharge from the EDA/PIP removal is typically introduced into a further distillation column (EDA removal), which is operated in such a way that EDA is obtained at the top of the column, and piperazine can be drawn off at the bottom of the column. The exact operating conditions of the distillation column can be determined according to the separating performance of the column used by the person skilled in the art with reference to the known vapor pressures and evaporation equilibria of the components introduced into the distillation column by conventional calculation methods in a routine manner.

The distillation column preferably has internals for increasing the separating performance. The distillative internals may be present, for example, as a structured packing, for example as a sheet metal packing such as MELLAPAK™ 250 Y sheet metal packing or Montz Pak, B1-250 type. It is also possible for a packing with a lower or increased specific surface area to be present, or it is possible to use a fabric packing or a packing with another geometry, such as MELLAPAK™ 252 Y sheet metal packing. Advantages in the case of use of these distillative internals are the low pressure drop and the low specific liquid holdup compared to valve trays, for example. The internals may be present in one or more beds.

The tops discharge from the EDA/PIP removal is preferably supplied within a spatial region between 25% and 75% of the theoretical plates of the distillation column (counted from the bottom), more preferably within a spatial region between 30% and 65% of the theoretical plates of the distillation column. For example, the supply may be slightly below the middle of the theoretical plates. The optimal feed point can be determined by the person skilled in the art with the customary calculation tools.

The number of theoretical plates is generally in the range from 10 to 70, preferably 20 to 50.

The top pressure is more preferably 0.1 to 10 bar, more preferably 0.5 to 5 bar. Very particular preference is given to operating the column at standard pressure.

In the column bottom, preference is given to establishing a temperature which is above the evaporation temperature of EDA but below the evaporation temperature of piperazine. For example, at a column top pressure of 1 bar (abs.), preferably a column bottom temperature of 120 to 200° C., more preferably of 140 to 160° C., can be established.

The condenser of the distillation column is generally operated at a temperature at which the predominant portion of the EDA-piperazine mixture is condensed at the corresponding top pressure. In general, the operating temperature of the condenser is in the range from 50 to 150° C., preferably 110 to 130° C.

The condensate obtained in the condenser is preferably recycled into the top of the distillation column to an extent of more than 30%, preferably to an extent of more than 50% by weight.

The energy required for the evaporation is typically introduced by means of an evaporator in the column bottoms.

In the bottoms discharge, piperazine is generally obtained.

In the condenser, a condensate is obtained, which comprises predominantly EDA, but only very small amounts of Me-EDA.

The condensate is generally predominantly free of higher-boiling amines, including piperazine. The proportion of higher-boiling amines, including piperazine, is generally less than 0.5% by weight, preferably less than 0.3% by weight and more preferably less than 0.2% by weight.

By means of the process according to the invention, it is possible to obtain a mixture of EDA and Me-EDA, said mixture comprising at least 99.5% by weight of EDA and the concentration of Me-EDA being less than 0.4% by weight, preferably less than 0.3% by weight, more preferably less than 0.2% by weight and especially preferably less than 0.1% by weight.

By means of the process according to the invention, it is possible to obtain a mixture of EDA and Me-EDA, said mixture comprising at least 99.5% by weight of EDA, and the concentration of Me-EDA being in the range from 0 to 0.4% by weight, preferably 0.005 to 0.3% by weight, more preferably from 0.01 to 0.15% by weight.

By means of the process according to the invention, it is also possible to obtain mixtures of EDA and Me-EDA which have a very low Me-EDA content.

Accordingly, the present invention also relates to a mixture of EDA and Me-EDA, which comprises at least 99.5% by weight of EDA, and wherein the concentration of Me-EDA is in the range from 0.005 to 0.15% by weight, preferably 0.008 to 0.1% by weight, and more preferably in the range from 0.01 to 0.05% by weight.

The inventive mixture is advantageously suitable for applications in which a very high purity of the EDA is important.

The inventive mixture can be used, for example, to produce high molecular weight polymers such as polyamides, since the functionality of the EDA is not reduced by the formation of Me-EDA. For example, the inventive mixture can also be used as an electronics chemical or as a high-purity chemical for use in the field of crop protection compositions, pesticides, epoxy resins, complexing agents, or for applications in the leather industry, the paper industry or the detergents industry. The use of high-purity chemicals increases the yield of end product, decreases the concentration of undesired by-products and can additionally lead to an improvement in the use and processing properties in the fields of use in question.

The inventive mixture can be prepared as described above, in which a mixture comprising EDA, Me-EDA and water is introduced into a distillation column for removal of Me-EDA which is operated at a column top pressure of 10 mbar to 4 bar, wherein the weight ratio of water to ethylenediamine in the mixture to be distilled is a*X:Y where X is the proportion by weight of water and Y is the proportion by weight of ethylenediamine at the azeotropic point of a binary mixture of water and EDA at the column top pressure in question, and a is a real number with a value of 0.9 or more, preferably 1.0 or more and more preferably 1.02 or more, and the bottoms discharge from the Me-EDA removal is introduced into a further distillation column for water removal, in which an aqueous distillate is obtained at the top, and a water-depleted bottom product, and the water-depleted bottom product from the water removal is introduced into one or more distillation stage(s) for EDA removal to obtain the inventive mixture at the top of the column or of one of the columns.

By means of the process according to the invention for removing Me-EDA from a mixture comprising EDA, Me-EDA and water, which is obtained in the preparation of EDA, it is possible to obtain on-spec EDA with a content of at least 99.5% by weight of EDA even when relatively large amounts of Me-EDA form in the preparation of EDA. This may be the case, for example, when EDA is prepared from C1 units, such as formaldehyde and hydrogen cyanide, or when catalysts exhibit partial deactivation with increasing operating time and the reaction temperature has to be increased to compensate for the deactivation. The increase in the temperature generally results in a deterioration in the selectivity in relation to the preparation of EDA, and increased formation of Me-EDA as a by-product. The process according to the invention thus also enables the use times of the catalysts in the preparation of EDA to be increased.

By means of the process according to the invention, it is additionally possible to obtain a high-purity EDA which can be used with improved yield and fewer side reactions as a starting material in a multitude of applications.

The process according to the invention is illustrated by the examples which follow.

EXAMPLE 1

Distillation According to the Prior Art

The discharge from the reactor of the ethyleneamine synthesis comprises 5.1% by weight of water, 11.7% by weight of EDA, 300 ppm by weight of Me-EDA, 1.2% by weight of piperazine, 9.6% by weight of monoethanolamine, 1.6% by weight of DETA, 2.3% by weight of ethyleneamines or high boilers having higher boiling points than DETA; the remainder is ammonia. After ammonia removal in a pressure distillation at 18 bar, water is removed via the top in a further pressure distillation with 50 theoretical plates at 8 bar. The bottoms discharge comprising the ethyleneamines comprises approx. 1200 ppm by weight of water and approx. 800 ppm by weight of Me-EDA. After further distillation steps under standard pressure, in which the amines are separated into the pure components, an EDA fraction is obtained with more than 99.5% by weight of EDA, approx. 2500 ppm by weight of water and 1800 ppm by weight of Me-EDA, i.e. the EDA fraction is on spec.

EXAMPLE 2

Distillation According to the Prior Art at Higher Me-EDA Content

The discharge from the reactor of the ethyleneamine synthesis comprises 5.1% by weight of water, 11.7% by weight of EDA, 1500 ppm by weight (or 2000 ppm by weight) of Me-EDA, 1.2% by weight of piperazine, 9.6% by weight of monoethanolamine, 1.6% by weight of DETA, 2.3% by weight of ethyleneamines or high boilers having higher boiling points than DETA; the remainder is ammonia. The composition corresponds substantially to example 1, except that the proportion of Me-EDA has increased to 1500 ppm by weight or 2000 ppm by weight. After ammonia removal in a pressure distillation at 18 bar, water is removed via the top in a further pressure distillation at 8 bar. With the same number of theoretical plates as in example 1, it is possible for both Me-EDA concentrations only with considerably higher energy expenditure to remove the water to such an extent that an on-spec EDA fraction with at least 99.5% by weight of EDA can finally be obtained. At the same time, the water distilled off is contaminated to a considerably higher degree with EDA and Me-EDA (approx. 5% by weight instead of 2000 ppm). At 2000 ppm by weight of Me-EDA in the reaction discharge, the required purity of EDA is achievable only with increased energy expenditure and acceptance of product loss (reduced EDA distillation yield). At the same time, the amine contamination of the water stream distilled off becomes increasingly greater and the disposal correspondingly more expensive, since the amine content (EDA and Me-EDA) reaches as much as 12% by weight, three quarters of which is EDA, at an Me-EDA content of 2000 ppm.

EXAMPLE 3

Inventive Distillation

The discharge from the reactor of the ethyleneamine synthesis comprises 5.1% by weight of water, 11.7% by weight of EDA, 1500 ppm by weight of Me-EDA, 1.2% by weight of piperazine, 9.6% by weight of monoethanolamine, 1.6% by weight of DETA, 2.3% by weight of ethyleneamines or high boilers having higher boiling points than DETA; the remainder is ammonia, i.e. the composition corresponds to example 2. After ammonia removal in a pressure distillation at 18 bar, a mixture of water (85% by weight), Me-EDA (14% by weight) and EDA (1.0% by weight) is first removed via the top in a distillation column at a top pressure of 100 mbar (abs.). At 0.1 bar (abs.), the binary EDA-water azeotrope is at approx. 27.3% by weight of water. The ratio of water to EDA in the feed stream of 5.1%:11.7%, i.e. 30.4% water based on the binary system, is higher than in the binary azeotrope. It is therefore unnecessary to supply further water to the distillation. In a subsequent pressure distillation with 50 theoretical plates, further water is removed via the top at 8 bar, analogously to example 1. The bottoms discharge comprising the ethyleneamines comprises approx. 1500 ppm by weight of water and approx. 40 ppm by weight of Me-EDA. After further distillation steps in which the amines are separated into the pure components, an EDA fraction is obtained with approx. 99.65% by weight of EDA, approx. 2900 ppm by weight of water and 90 ppm by weight of Me-EDA, i.e. the EDA fraction is on spec. At the same Me-EDA content in the reactor discharge as in example 2, a higher purity of EDA is achieved, the total amount of energy expended being less than in example 2. The water removal can be conducted in a less sharp manner compared to example 1 or 2. Barely any EDA is lost via the wastewater stream.

EXAMPLE 4

Inventive Distillation of an Me-EDA-Comprising Mixture of Ethyleneamines

A mixture comprises 18.2% by weight of water, 72.7% by weight of EDA, 9.1% by weight of Me-EDA. At 0.1 bar (abs.), the binary EDA-water azeotrope is at approx. 27.3% by weight of water. The ratio of water to EDA at the azeotropic point is thus 27.3/(100-27.3)=0.375. The ratio of water to EDA in the feed stream of 18.2%:72.7%=0.250 (20.0% water based on the binary system) is lower than in the binary azeotrope. An inventive separation is thus not possible. Further water is therefore added to the feed, specifically 13 parts by weight based on the abovementioned feed stream, i.e. a further 130 kg/h of water are added to a feed stream of 1000 kg/h (i.e. comprising 182 kg/h of water and 727 kg/h of EDA therein). In total, 312 Kg/h of water are thus present in the feed. In accordance with the invention, the ratio of water to EDA is 312:727=0.429 (30.0% based on the binary system). The ratio of water to EDA in the feed stream then corresponds to a=1.14 times the ratio of water to EDA at the azeotropic point. The top product stream of the column comprises approx. 35% by weight of water, 1% by weight of EDA and 64% by weight of Me-EDA. The bottom product stream comprises approx. 26.6% by weight of water, 73.3% by weight of EDA and 0.1% by weight of Me-EDA. In a subsequent pressure distillation with 30 theoretical plates, further water is removed via the top at 14 bar (abs.). The bottoms discharge comprises approx. 99.66% by weight of EDA, 2500 ppm by weight of water and approx. 900 ppm by weight of Me-EDA.

EXAMPLE 5

Inventive Distillation of an Me-EDA-Comprising Mixture of Ethyleneamines

A mixture comprises 18.2% by weight of water, 72.7% by weight of EDA, 9.1% by weight of Me-EDA. The intention is to separate at standard pressure in such a way that the EDA fraction comprises at least 99.5% by weight of EDA. At 1 bar (abs.), the binary EDA-water azeotrope is at approx. 14.7% by weight of water. The ratio of water to EDA at the azeotropic point is 14.7/(100−14.7)=0.172. The ratio of water to EDA in the feed stream of 18.2%:72.7%=0.250 (20.0% water based on the binary system) is higher than in the binary azeotrope. The ratio of water to EDA in the feed stream then corresponds to a=1.45*the ratio of water to EDA at the azeotropic point. It is therefore not necessary to add any further water to the feed. The top product stream of the column comprises approx. 38.9% by weight of water, 1% by weight of EDA and 60.1% by weight of Me-EDA. The bottom product stream comprises approx. 14.5% by weight of water, 85.4% by weight of EDA and 0.1% by weight of Me-EDA. In a subsequent pressure distillation with 30 theoretical plates, further water is removed via the top at 14 bar (abs.). The bottoms discharge comprises approx. 99.65% by weight of EDA, 2500 ppm by weight of water and approx. 1000 ppm by weight of Me-EDA. Instead of via the bottom, the EDA fraction can be obtained in virtually the same purity via a vaporous side draw in the stripping section of the column.

The invention claimed is:

1. A process for distilling a mixture comprising water, ethylenediamine and N-methylethylenediamine, by introducing the mixture into a distillation column which is operated at a column top pressure of 10 mbar to 4 bar, wherein the weight ratio of water to ethylenediamine in the mixture used is a·X:Y where X is the proportion by weight of water and Y is the proportion by weight of ethylenediamine at the azeotropic point of a binary mixture of water and ethylenediamine at the column top pressure in question, and a is a real number with a value of 0.9 or more.

2. The process according to claim 1, wherein a is a real number with a value of 1.01 to 1.2.

3. The process according to claim 1, wherein the mixture used in the process comprises less than 5% by weight of ammonia.

4. The process according to claim 1, wherein the weight ratio of ethylenediamine to N-methylethylenediamine in the mixture used is in the range from 1:0.005 to 1:0.1.

5. The process according to claim 1, wherein the column top pressure is 50 mbar to 200 mbar.

6. The process according to claim 1, wherein the column top pressure is atmospheric pressure.

7. The process according to claim 1, wherein the mixture used in the process also comprises further amines which have a higher boiling point than ethylenediamine, where the weight ratio of ethylenediamine to the higher-boiling amines is in the range from 1:0.1 to 1:1.

8. The process according to claim 1, wherein the mixture used in the process has been obtained from the conversion of ethylenediamine from ethanolamine and ammonia.

9. The process according to claim 1, wherein the mixture used in the process has been obtained from the conversion of formaldehyde, hydrogen cyanide, ammonia and hydrogen.

10. A process for preparing a distillable mixture comprising ethylenediamine and N-methylethylenediamine, which comprises adding a sufficient amount of water to a mixture comprising ethylenediamine and N-methylethylenediamine that, after the addition of water, the weight ratio of ethylenediamine to water is a·X:Y where X is the proportion by weight of water and Y is the proportion by weight of ethylenediamine at the azeotropic point of a binary mixture of water and ethylenediamine at the column top pressure at which a subsequent distillation of the distillable mixture according to claim 1 can be effected, and a is a real number with a value of 0.9 or more.

11. The process according to claim 10, wherein the distillable mixture is distilled in a distillation column at a pressure of 20 mbar to 2 bar.

12. A process for preparing a mixture of ethylenediamine and N-methylethylenediamine, which comprises at least 99.5% by weight of ethylenediamine, and wherein the concentration of N-methylethylenediamine is in the range from 0.005 to 0.15% by weight, in which a mixture comprising ethylenediamine, N-methylethylenediamine and water is introduced into a distillation column for removal of N-methylethylenediamine which is operated at a column top pressure of 10 mbar to 4 bar, wherein the weight ratio of water to ethylenediamine in the mixture used in the process is a·X:Y where X is the proportion by weight of water and Y is the proportion by weight of ethylenediamine at the azeotropic point of a binary mixture of water and ethylenediamine at the column top pressure in question, and a is a real number with a value of 0.9 or more, and the bottoms discharge from the N-methylethylenediamine removal is introduced into a further distillation column for water removal, in which an aqueous distillate is obtained at the top, and a water-depleted bottom product, and the water-depleted bottom product from the water removal is introduced into one or more distillation stage(s) for EDA removal to obtain the inventive mixture at the top of the column or of one of the columns.

* * * * *